United States Patent [19]

Kimura et al.

[11] Patent Number: 5,417,680
[45] Date of Patent: May 23, 1995

[54] DISPOSABLE DIAPERS

[75] Inventors: Noriyuki Kimura, Iyomishima; Yoshihisa Fujioka, Kagawa; Hirotomo Mukai, Kawanoe, all of Japan

[73] Assignee: Uni-Charm Corporation, Ehime, Japan

[21] Appl. No.: 201,321

[22] Filed: Feb. 24, 1994

[30] Foreign Application Priority Data

Mar. 5, 1993 [JP] Japan .................................. 5-045329

[51] Int. Cl.6 ................................................ A61F 13/15
[52] U.S. Cl. ................................... 604/385.2; 604/358
[58] Field of Search .................. 604/358, 385.1, 385.2, 604/393-397

[56] References Cited

U.S. PATENT DOCUMENTS

| 4,265,245 | 5/1981 | Glassman | 604/397 |
| 5,236,428 | 8/1993 | Zajaczkowitz | 604/385.1 |
| 5,360,422 | 11/1994 | Brownlee et al. | 604/385.2 |

FOREIGN PATENT DOCUMENTS

| 2144995 | 3/1985 | United Kingdom . |
| 2269999 | 3/1994 | United Kingdom . |

Primary Examiner—Randall L. Green
Assistant Examiner—Rob Clarke
Attorney, Agent, or Firm—Lowe, Price, LeBlanc & Becker

[57] ABSTRACT

A disposable diaper comprises an auxiliary pad being deformable to present an inverted Ω-shaped cross-section and bonded at its central portion to a crotch zone of the diaper 4 Claims, 2 Drawing Sheets

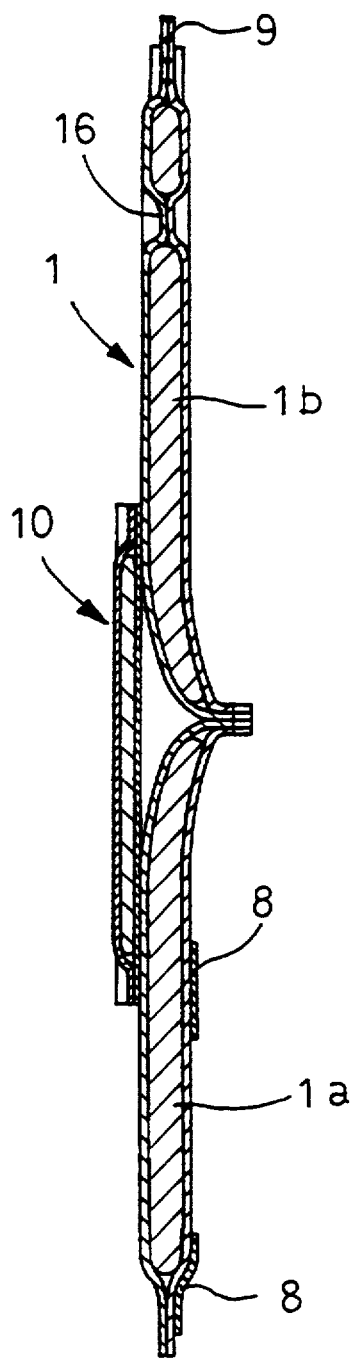
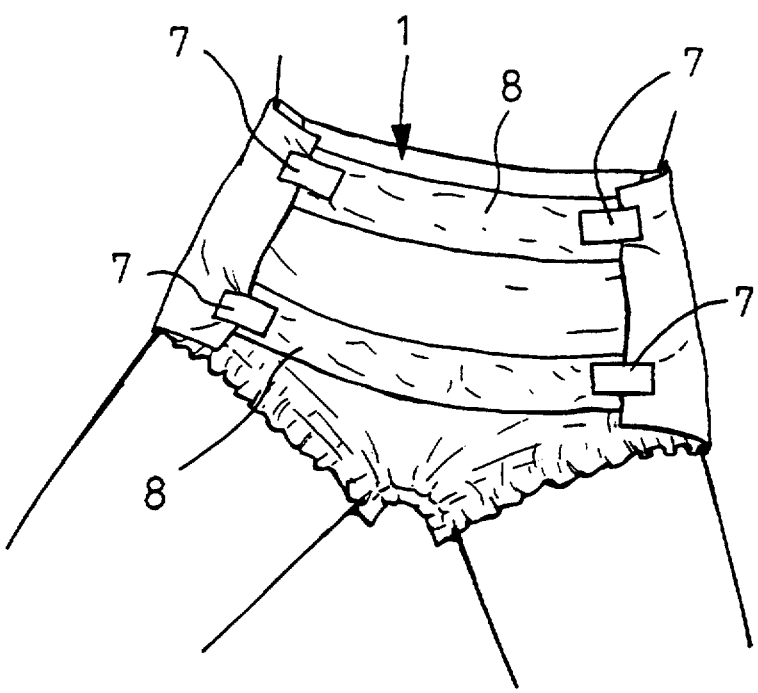

DISPOSABLE DIAPERS

BACKGROUND OF THE INVENTION

The present invention relates to a disposable diaper used for the absorption and containment of body excretions.

Various proposals have already been made for disposable diapers comprising a liquid-permeable topsheet, a liquid-impermeable backsheet, an absorbent panel sandwiched between these sheets, notches formed in opposite sides of a crotch region destined to define leg-openings, stretchable elastic means provided adjacent respective side edges of said notches, and flaps provided on opposite sides of said topsheet adapted to rise under the contraction of elastic means in order to prevent body excretions from leaking in the lateral direction.

However, said flaps of well known art are provided along their full length integrally with said topsheet so that these flaps are stretched or contracted as the regions of the diaper surrounding the wearer's legs are stretched or contracted. In consequence, said flaps slack as the leg-openings of the diaper slack, often resulting in leakage of body excretions. Even if leakage of body excretions in the lateral direction can be prevented by these flaps, a region of the diaper extending between these flaps spaced from each other allows body excretions to spread over its relatively large extent and feces would contaminate the wearer's skin at least over this region.

It is a principal object of the invention to solve such a problem by attaching an auxiliary pad dimensioned to cover said crotch zone, i.e., to cover anus and urinary organs of the wearer on said topsheet so that the auxiliary pad is not directly affected by the movement of said leg-openings.

SUMMARY OF THE INVENTION

The object set forth above is achieved, according to the invention, by a disposable diaper comprising a diaper having a liquid-permeable topsheet, a liquid-impermeable backsheet, an absorbent panel sandwiched between these sheets, notches formed in opposite sides of a crotch zone of said diaper, said notches being destined to define leg-openings of said diaper, and stretchable means provided adjacent side edges of said notches, said disposable diaper including an auxiliary pad provided separately of said diaper dimensioned so as to cover a crotch zone of the diaper and bonded to an upper surface of said topsheet with opposite outer side regions of said auxiliary pad being left free, said auxiliary pad being provided with longitudinally stretchable elastic members extending substantially in parallel with and spaced inward from said opposite outer side regions so that said auxiliary pad may be deformed to present an inverted $\Omega$-shaped cross-section as said elastic members contract.

Preferably, said auxiliary pad comprises a liquid-permeable upper sheet, a liquid-impermeable lower sheet and a liquid absorbent panel sandwiched between these sheets.

In use of the diaper the auxiliary pad is deformed to present the inverted $\Omega$-shaped cross-section under the contracting effect of the elastic members provided on the opposite sides thereof. Excretion is preferentially and easily caught by the auxiliary pad thus deformed in the inverted $\Omega$-shape. The auxiliary pad is fixed only at its central portion of the diaper and therefore is always stabilized over anus and urinary organs of the wearer without being directly affected by the movement of the leg-openings of the diaper.

BRIEF DESCRIPTION OF THE DRAWINGS

The invention will be described more in detail by way of example in reference with the accompanying drawings, in which:

FIG. 3 is a view similar to FIG. 2 but taken along a line Y—Y in FIG. 1; and

FIG. 4 is a perspective view showing said diaper as put on a wearer.

PREFERRED EMBODIMENTS OF THE INVENTION

Figure 1:
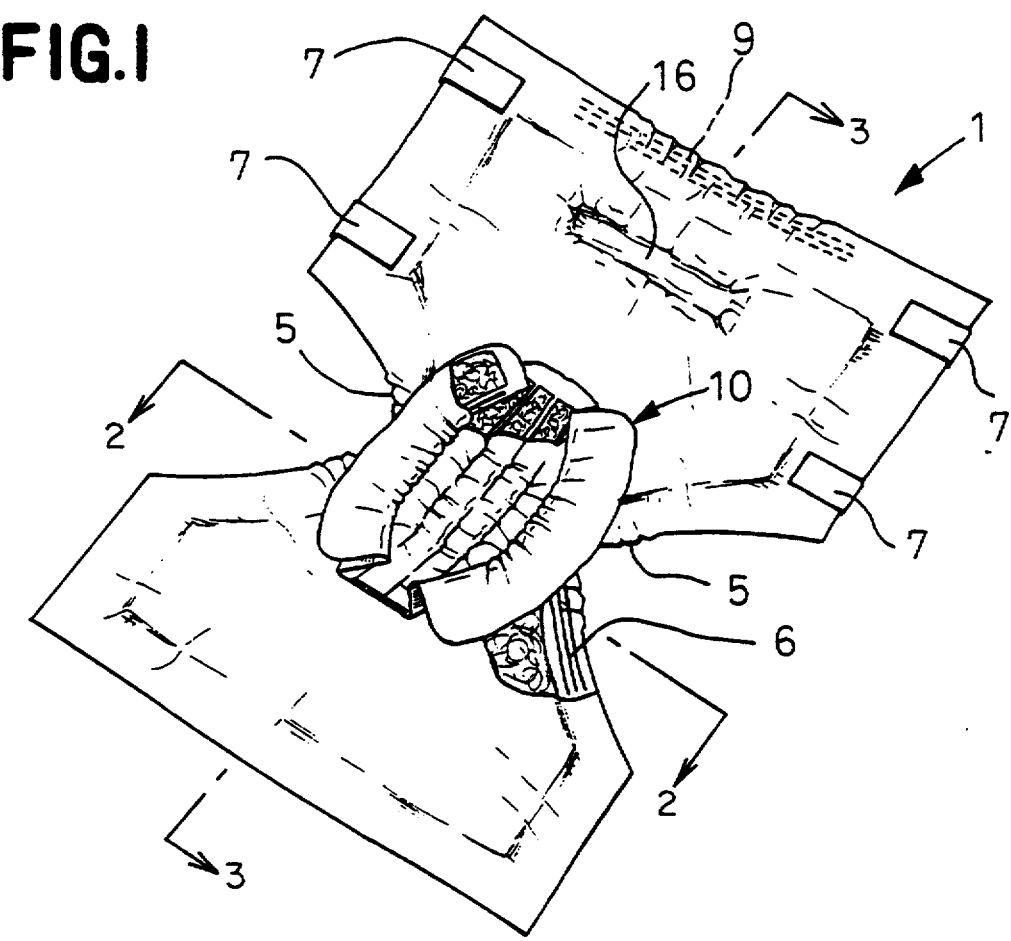
FIG. 1 is perspective view showing an inner side of a diaper constructed according to the invention.
Figure 2:
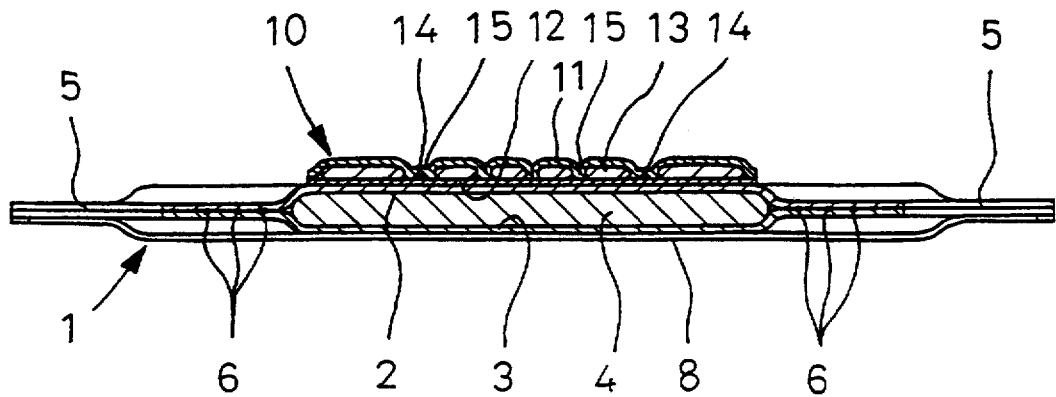
FIG. 2 is a sectional view showing, in an enlarged scale, said diaper as stretched both in length and width along a line X—X in FIG. 1.

Referring to FIGS. 1 and 2, a diaper 1 comprises a liquid-permeable topsheet 2, a liquid-impermeable backsheet 3, an absorbent panel 4 sandwiched between these sheets 2, 3 bonded together along their outer peripheral edges, notches 5 formed in opposite sides of a crotch zone, said notches 5 being destined to define respective leg-openings, longitudinally stretchable elastic members 6 interposed between said two sheets adjacent side edges of the respective notches 5 and tape fasteners 7 fixed to opposite sides of a rear body. To an outer surface of a front body onto which a free end of each tape fastener 7 is to be bonded, pieces of reinforcing tape 8 extending transversely of said outer surface are bonded (See FIGS. 3 and 4). The rear body of the diaper 1 is provided along its rear end with a transversely stretchable elastic member 9 sandwiched between said two sheets. Adjacent this elastic member 9, a compressed groove 16 transversely extends in parallel thereto.

On the top surface of the topsheet 2 in the crotch zone of the diaper 1, there is provided an auxiliary pad 10 dimensioned and configured so as to cover the crotch zone and anus and urinary organs of the wearer. The auxiliary pad 10 comprises a liquid-permeable upper sheet 11, a liquid-impermeable lower sheet 12 and a liquid-absorbent panel 13 thinner than the panel 4 and sandwiched between these sheets 11, 12 which are, in turn, bonded together along their outer peripheral edges, and longitudinally stretchable elastic members 14 sandwiched between said sheets 11, 12 and extending substantially in parallel to and spaced inward from the respective opposite side regions each having a desired width. The auxiliary pad 10 has longitudinally extending compressed grooves 15 immediately on lines corresponding to the respective elastic members 4 and also in a space defined between these two lines, and bonded to the topsheet 2 over a longitudinally central portion. Accordingly, when the elastic members 14 contract, the laterally opposite regions of the auxiliary pad 10 are curved in an inverted V-shape with their apices being formed by said lines defined by the respective elastic members 14, and the auxiliary pad 10 as a whole is deformed to present an inverted $\Omega$-shaped cross-section as will be best seen in FIG. 1. While the formation of the compressed grooves 15 immediately on the lines of the elastic members 14 facilitates the pad 10 to be curved along these lines in the inverted V-shape with their apices being defined by these lines, the pad 10 will be curved substantially in the same manner even when no groove 15 is provided on each line. Width of the auxiliary pad 10 is preferably dimensioned so that the opposite side edges of said pad 10 may extend outward from the most deep portions of the respective notches over an appropriate extent when said pad 10 has been deformed into the inverted Ω-shape.

Referring to FIG. 3, the diaper 1 comprises a front body 1a and a rear body 1b connected to each other along respective one ends thereof. Said auxiliary pad 10 is bonded to the topsheet 2 over the crotch zone of the diaper 1 and longitudinally extends across the boundary of said front and rear bodies 1a, 1b. Although such an arrangement is not a part of this invention, the arrangement conveniently allows, for example, the front and rear bodies 1a, 1b to be made from material of types different from each other so that the air-permeability and liquid-absorptivity of the front body 1a may be different from those of the rear body 1b. While the diaper 1 arranged in such a manner is disadvantageous in that the absorptivity for excretion is necessarily low on the boundary of these two bodies 1a, 1b, such a problem can be overcome by the auxiliary pad 10 bonded to the topsheet 2 over the area in question.

The topsheet 2 and the upper sheet 11 may be made of nonwoven fabric, the backsheet 3 and the lower sheet 12 may be made of plastic film, the panels 4, 13 may be made of fluff pulp mixed with superabsorption polymer particles, and the elastic members 6, 9, 14 may be made of rubber or elastomer having a rubber-like elasticity.

According to the embodiments of the invention, the auxiliary pad 10 deformed into a container having said inverted Ω-shape as the diaper 1 is put on the wearer as shown by FIG. 4 completely covers anus and urinary organs of the wearer with the opposite outer side regions being pressed against such area under the effect of not only the elastic members 14 but also the elastic members 6 provided around the leg-openings. In other words, the auxiliary pad 10 serves as a pocket catching and holding body excretions so as not to leak along the outer periphery of said pad 10.

According to the invention, the auxiliary pad reliably catches excretion and prevents body excretions from spreading within the diaper over its relatively large extend and contaminating the wearer's skin. In addition, the auxiliary pad 10 is not directly affected by the movement of the diaper's opposite outer sides and reliably holds body excretions once caught therein. Accordingly, even if the opposite sides of the diaper slacken, no leakage of body excretions occurs from opposite sides of the crotch zone.

What is claimed is:

1. A disposable diaper, comprising a liquid-permeable topsheet, a liquid-impermeable backsheet, an absorbent panel sandwiched between said sheets, notches formed in opposite sides of a crotch zone defined by said sheets, said notches defining leg-openings of said diaper when being worn, and stretchable means provided adjacent side edges of said notches, said disposable diaper further including an auxiliary pad containing at least one absorbent panel, said auxiliary pad being dimensioned to cover a crotch zone of said diaper and being bonded to an upper surface of said topsheet, said auxiliary pad being provided with longitudinally stretchable elastic members extending substantially in parallel with and spaced inward from said opposite outer side regions so that said at least one absorbant panel deforms to present an inverted Ω-shaped cross-section in the width direction as said elastic members contract.

2. A disposable diaper, comprising a liquid-permeable topsheet, a liquid-impermeable backsheet, an absorbent panel sandwiched between said sheets, notches formed in opposite sides of a crotch zone defined by said sheets, said notches defining leg-openings of said diaper when being worn, and stretchable means provided adjacent side edges of said notches, said disposable diaper further including an auxiliary pad containing at least one absorbent panel, said auxiliary pad being dimensioned to cover a crotch zone of said diaper and being bonded to an upper surface of said topsheet with opposite side regions of said auxiliary pad being left free, said auxiliary pad being provided with longitudinally stretchable elastic members extending substantially in parallel with and spaced inward from said opposite outer side regions so that said at least one absorbent panel deforms to present an inverted Ω-shaped cross-section in the width direction as said elastic members contract.

3. A disposable diaper according to claim 2, wherein said auxiliary pad comprises a liquid-permeable upper sheet, a liquid-impermeable lower sheet and a liquid absorbent panel sandwiched between said sheets.

4. The disposable diaper of claim 2, wherein each said opposite side region includes an upstanding portion extending upward from the topsheet and terminating in an outwardly extending portion extending laterally toward an adjacent one of said notches and above said upstanding portion.

* * * * *